United States Patent [19]
Cannon

[11] B 3,981,309
[45] Sept. 21, 1976

[54] PATIENT STIMULATING PACER ELECTRODE

[75] Inventor: Robert Lee Cannon, Waltham, Mass.

[73] Assignee: American Optical Corporation, Southbridge, Mass.

[22] Filed: Dec. 23, 1974

[21] Appl. No.: 535,466

[44] Published under the second Trial Voluntary Protest Program on January 27, 1976 as document No. B 535,466.

[52] U.S. Cl. .............................. 128/419 P; 128/404
[51] Int. Cl.² .......................................... A61N 1/04
[58] Field of Search ........ 128/404, 417, 418, 419 P, 128/DIG. 4

[56] References Cited
UNITED STATES PATENTS

| | | | |
|---|---|---|---|
| 2,895,479 | 7/1959 | Lloyd | 128/417 |
| 3,476,116 | 11/1969 | Parsonnet et al. | 128/419 P |
| 3,478,746 | 11/1969 | Greatbatch | 128/419 PG |
| 3,533,403 | 10/1970 | Woodson | 128/419 P |
| 3,572,344 | 3/1971 | Bolduc | 128/419 P |
| 3,749,101 | 7/1973 | Williamson | 128/419 P |
| 3,804,098 | 4/1974 | Friedman | 128/419 P |

*Primary Examiner*—William E. Kamm
*Attorney, Agent, or Firm*—Howard R. Berkenstock, Jr.; William C. Nealon

[57] ABSTRACT

A patient stimulating pacer electrode for use with heart pacers or other like devices. The electrode is constructed in a porous manner to have large surface area to reduce polarization losses while simultaneously having small overall dimensions for increasing stimulation current density and its ability to stimulate. Electrically conductive powdered metal is subjected to a sintering process to produce a porous conductive structure which is employed as the electrode. Conductive fluid from within the patient's body flows into the interstices of the overall small-dimensioned porous conductive structure; the resulting fluid-structure interface comprises a large surface area thereby reducing polarization losses.

2 Claims, 3 Drawing Figures

PATIENT STIMULATING PACER ELECTRODE

BACKGROUND OF THE INVENTION

1. Field of the Invention

The present invention relates generally to an improved electrode for use in electrical stimulation of patient muscle tissue for therapeutic purposes. More specifically, the present invention relates to an improved electrode for use with electronic heart pacers.

2. Description of Prior Art

Prior art electrodes are related to means for conducting electrical current to and from patient muscle tissue by contact between tissue and electrode at some uncontrollable, unspecified point or surface area of the electrode. Prior art electrodes normally are constructed to have smooth surfaces and are generally shaped in cylindrical-like configurations. Examples of prior art electrodes can be seen in U.S. Pat. Nos. 3,729,008 and 3,825,015. Background subject matter disclosed in these patents is incorporated herein by reference.

A shortcoming of prior art electrodes is that they cannot simultaneously solve two physiologically-related stimulation problems which confront devices which are employed to stimulate via electrodes. The first physiological constraint is that the stimulation threshold presented to a pacer electrode is directly proportional to electrode area in constant with patient tissue. In other words, the larger the contact area between heart tissue and electrode surface, the lower the current density and the higher the stimulation threshold. Thus, by reducing size of electrodes, current density can be increased.

However, polarization losses, the losses which are due to the build-up of charge at the interface between the tissue and the electrode surface and poled in a direction to oppose current flow, are inversely proportional to total electrode area. Therefore, if one designs an electrode to be small in surface area to achieve high current density, then the polarization losses may become excessive and prohibit efficient operation of a stimulating system. This has been and still is a problem of prior art electrodes.

The present invention provides a solution to this problem of the prior art. The present invention provides structure for simultaneously solving both problems, and is thereby a major advance over prior art electrodes.

SUMMARY OF THE INVENTION

The present invention relates to an electrode system capable of use with an electronic heart pacer. The electronic heart pacer and electrode system may be capable of implantation within the body of a patient. The electrode system is constructed from at least one insulated electrical conductor connected between pacer output and muscle tissue to be stimulated, and in this particular instance the heart muscle. The electrically-conductive tissue-contacting distal end of the electrode is constructed to be a rigid but porous electrical conductor, and can be constructed from platinum dust. The resulting porous structure provides a large area of contact between electrode structure and body fluids, thereby providing an overall large electrode surface area contact to reduce polarization problems, while simultaneously permitting reduction in overall electrode dimensions to increase current density at the area of contact between tissue wall and electrode structure.

An advantage, among other, of the present invention is that it permits longer periods of implantable pacer use than otherwise available, because the ever-depleting energy of implanted batteries is used more efficiently. The stimulation threshold is lower due to high current density, and at the same time the polarization losses are minimized due to a large electrode surface area. With conventional electrodes, a typical stimulation threshold is two or three milliamps of current for a duration of one millisecond. This current level and time duration represent about 75% of the current drain from a typical implantable pacer's batteries. The present invention can reduce the 75% current drain figure to about 25% or less.

It is therefore an object of the present invention to provide an improved muscle-stimulating electrode system.

It is another object of the present invention to provide an improved electrode for stimulating the heart of a patient.

It is further object of the present invention to provide an improved heart pacer system.

It is yet another object of the present invention to provide an improved electrode pacer system which can simultaneously optimize heart stimulation threshold requirements and polarization losses.

Other objects and advantages of the present invention will be understood after referring to the description of the preferred embodiments in connection with the following drawings wherein:

DESCRIPTION OF THE PREFERRED EMBODIMENTS

Figure 1:
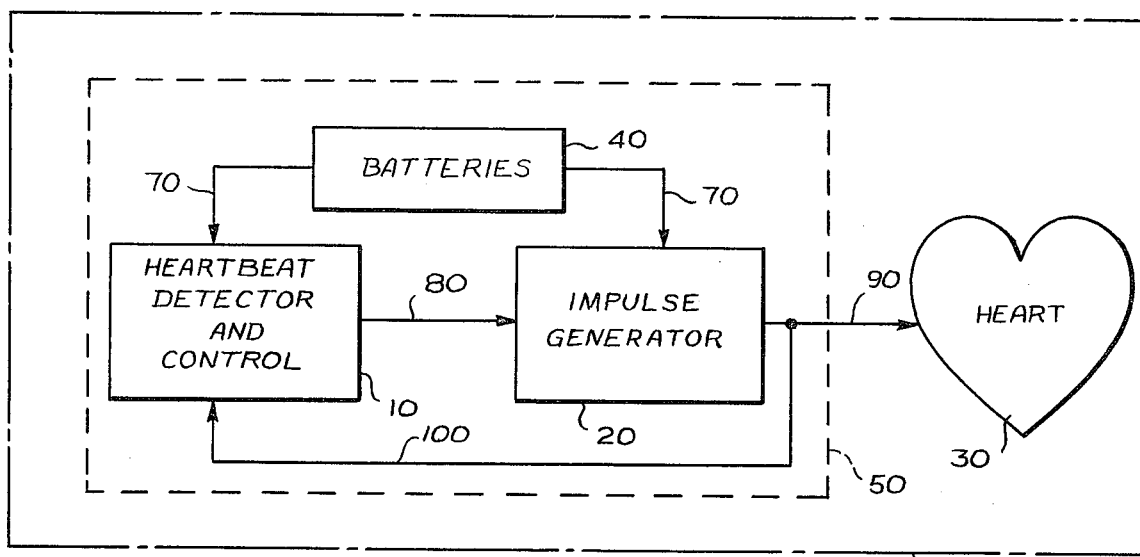
FIG. 1 depicts a typical heart pacer system.

Referring to FIG. 1, heartbeat detector and control 10, impulse generator 20, and batteries 40 are represented as being enclosed by dashed line 50. Dashed line 50 is intended to represent the outline of heart pacer encapulation suitable for implanting its enclosed electrical structure within the body of a patient. The structure within encapsulation 50, is shown in functional connection with patient's heart 30. Phantom line 60 is thus intended to represent the outline of the body of the patient.

Impulse generator 20 provides stimulation to heart 30 over electrode system or catheter system 90. Heartbeat detector and control 10 is connected to impulse generator 20 by electrical conductors 80. Batteries 40 power heartbeat detector and control 10 and impulse generator 20 over conductors 70. Conductors 100 are electrically connected to the heart and provide heartbeat signals to detector and control 10. U.S. Pat. No. 3,528,428, discloses pertinent subject matter, describes operation of such a pacing system, and is incorporated herein by reference.

Figure 2:
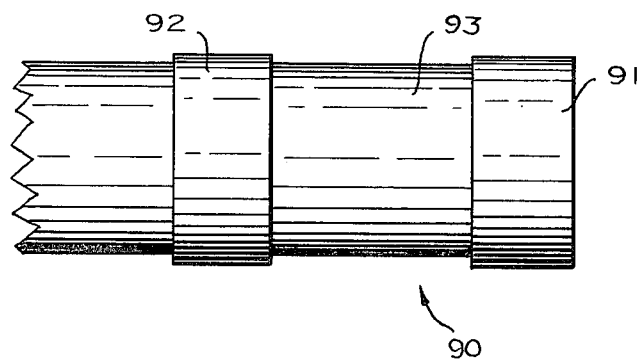
FIG. 2 depicts a side view of the tissue-contacting cylindrical distal tip of the electrode system employed in FIG. 1.

FIG. 2 depicts a tissue-contacting distal end portion of a catheter system of the prior art. Electrode 91 and 92 are exposed conductive metal cylindrical structures whose surface portions contact tissue surface of the heart at two separate, contact areas or points. Conductors 91 and 92 provide current flow paths to and from the heart. Each of these electrodes are electrically connected to conductors (not shown) within the cylindrical hollow of catheter system 90. These conductors are mutually insulated from each other, and may be constructed from coiled springs or other suitable configurations. Body-compatable material 93 is generally constructed from silastic rubber and provides insulation between the enclosed conductors and the patient's blood-vessel environment outside of enclosure 93.

The surface of conductors or electrodes 91 and 92 are solid and smooth. The problems associated with solid, smooth surfaces of these electrodes have been outlined earlier. Briefly, stimulation threshold presented to a pacer electrode is proportional to area of the tissue-electrode contact. Current density decreases as contact area increases, and the lower the current density, the more difficult stimulation can become. However, polarization losses, losses due to a reverse build up of potential at the interface between electrode and heart tissue, are inversely proportional to area of the interface.

Figure 3:
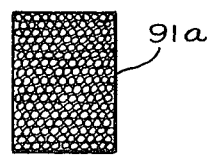
FIG. 3 depicts an illustrative embodiment of the present invention.

Referring to FIG. 3, an illustrative embodiment of the present invention is presented. This is a side view of another cylindrical electrode 91a similar to but smaller than electrode 91 of FIG. 2. The important diffrences are the electrode 91a is smaller than electrode 91 and that the structure of 91a has an interstitial character constructed by a sintering process, or other suitable process. The resulting porous structure has a very high multiplicity of interstices thus providing much larger surface area than otherwise available from a solid-surfaced electrode of approximately equal overall dimensions. The body fluids in the blood vessel or other internal environment in which the electrode system is placed flow into the interstices, thereby providing an overall large contact area between the electrode surface and the fluid and/or tissue. This large contact area reduces polarization losses between the metal electrode and its environment. Because of the substantially increased (cavernous) surface area due to porosity, the overall dimensions of the electrode are reduced in order to increase current density at the contact surface between tissue and electrode structure. Reduction of the overall dimensions of the porous electrode of the present invention from a first electrode size does not result in an electrode surface area smaller than that area provided by a solid electrode of the first size.

This electrode of the present invention is constructed from metallic dust, for example platinum dust, that is compressed or sintered under a high pressure process, resulting in welds at certain points between the dust particles that come in contact with one another. The pressure, temperature, and other process variables are controlled to provide a metal structure having residual inner spaces, and not to permit a flow of the metal dust into a solid structure. This sintering process is a form of a welding process. The resultant surface area is textured similarly to that of a cube of granulated sugar, for example. The resultant metallic conductor is then merely employed in place of the prior art smooth surface conductor 91 and the optimum result of the present invention is thereby achieved.

The invention may be embodied in yet other specific forms without departing from the spirit or essential characteristics thereof. Thus, the present embodiments are to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A heart pacer for stimulating the heart of a patient, said pacer comprising terminal means for connection to said patient's heart, generator means for providing stimulation impulses on said terminal means, means for detecting beating action of said patient's heart, means responsive to operation of said detecting means for controlling said generator means, means for energizing seriatim said generator means, said controlling means, and said detecting means, said terminal means comprising at least one insulated electrical conductor having two distal ends, one of said distal ends being electrically connected to and physically connected adjacent said generator means, the other of said distal ends being electrically connected to and physically contacting with tissue of said heart, said other distal end including electrically conductive porous means having point contact-welded matallic dust particles for conducting current through said heart tissue in a manner to decrease polarization losses between said porous means and its environment and simultaneously increase current density at the interface of said tissue and said porous means.

2. An electrode system capable of use with an electronic heart pacer, said system comprising at least one insulated electrical conductor whose distal ends are electrically connected between electrical output of said pacer and tissue of said heart, said tissue-connected distal end comprising electrically conductive porous means having point contact-welded metallic dust particles for conducting current from said pacer into said tissue in a manner to simultaneously decrease polarization losses and increase current density at the interface of said tissue and said conducting means.

* * * * *